United States Patent [19]

Olson

[11] Patent Number: 4,940,457
[45] Date of Patent: Jul. 10, 1990

[54] IRRIGATION SYSTEM FOR USE DURING ARTHROSCOPY

[75] Inventor: Daniel H. Olson, Louisville, Ohio

[73] Assignee: Snyder Laboratories, Inc., Dover, Ohio

[21] Appl. No.: 137,138

[22] Filed: Dec. 23, 1987

[51] Int. Cl.⁵ .............................................. A61M 1/00
[52] U.S. Cl. ...................................... 604/30; 604/122; 604/247
[58] Field of Search .................... 604/31, 30, 119, 122, 604/123, 247, 283, 22, 27, 29, 32-35; 128/66, 6

[56] References Cited

U.S. PATENT DOCUMENTS

| | | | |
|---|---|---|---|
| 274,447 | 3/1883 | Kennish | 604/247 |
| 4,461,281 | 3/1984 | Carson | 128/3 |
| 4,535,818 | 8/1985 | Duncan et al. | 604/122 |
| 4,555,645 | 11/1985 | Atkinson | 310/27 |
| 4,561,431 | 12/1985 | Atkinson | 128/66 |
| 4,635,621 | 1/1987 | Atkinson | 128/66 |
| 4,650,461 | 3/1987 | Woods | 604/30 |
| 4,662,871 | 5/1987 | Rafelson | 604/119 |
| 4,671,786 | 6/1987 | Krug | 604/247 |

OTHER PUBLICATIONS

3M Surgeon's Guide 3M Arthroscopy Pump (1986).
3M Operators Manual 3M Arthroscopy Pump (1986).
Orthopaedic Products Technical Bulletin #110 3M (3-1987).

Primary Examiner—Stephen C. Pellegrino
Attorney, Agent, or Firm—Paul D. Schoenle

[57] ABSTRACT

An irrigation system for arthroscopy of a joint includes a high pressure bleed valve assembly and a monitor check valve assembly to control fluid communication to the joint via suitable tubing for the purposes of directing fluid inflow, joint fluid pressure monitoring, and to assist with connection of the tubing for an arthroscope and cannula inserted into the joint. The high pressure bleed valve assembly is pressure responsive to direct fluid to the joint via alternative paths.

6 Claims, 3 Drawing Sheets

PRIOR ART
FIG. I

IRRIGATION SYSTEM FOR USE DURING ARTHROSCOPY

The present invention relates to an irrigation system for use during arthroscopy so that fluid is communicated to a joint to maintain a selected pressure level within the joint and to maintain a fluid flow as outflow is required.

In arthroscopic surgery, an arthroscope is used to visually inspect a joint, such as a knee or shoulder joint. It is possible to conduct diagnostic testing by viewing tissue, cartilage, etc. within the joint. If surgery is necessary to remove damaged tissue, for example, the arthroscope is used to view the resection of such damaged tissue by a shaver or suction punch well known to those skilled in the art. To assist the arthroscopic surgeon, fluid is communicated to the joint to pressurize the joint and thereby extend or expand the joint to enhance visual inspection. With the joint extended the arthroscope can be more readily orientated within the extended joint to focus on the damaged tissue.

A fluid circuit is used to communicate fluid from a reservoir to the joint via a control unit. The control unit includes a pump and a pressure transducer which is pressure responsive to control the operation of the pump. To prevent the introduction of air into the joint, the fluid circuit is initially a closed loop system such that operation of the pump purges all the air from the fluid circuit and primes the latter with fluid. Thereafter a portion of the fluid circuit is cut to provide two tubular openings, one for fluid inflow and the other for pressure monitoring, and these tubular openings are communicated with the joint.

During pump operation, fluid is communicated from the reservoir to the joint via an inflow path connected to an inflow cannular or to the arthroscope. The pressure monitor line is normally connected to a pressure monitor cannula. If the inflow path is crimped, restricted, or the arthroscope fluid passage is closed, restricted communication between the reservoir and the joint occurs. The pump operates in response to the pressure transducer sensing a low pressure level within the joint. However, with the inflow to the arthroscope closed, or restricted, fluid communicates to a safety relief valve with inadequate fluid communication to the joint as desired. Moreover, with gravity and earlier irrigation systems attached to the arthroscope, fluid communication is lost during arthroscope changes and repositioning because the fluid inflow valve on the arthroscope is normally turned off. This maneuver allows fluid to escape the joint and thus allow air to enter the joint causing vision-impaired air bubbles when the arthroscope is reinserted into the joint.

The present invention avoids the foregoing problems in a fluid circuit for arthroscopy. A fluid circuit according to the present invention includes a monitor check valve assembly (MCV) at the location of the fluid circuit which is to be cut or separated so that one of the two tubular openings provided after such cutting is closed and the other tubular opening is provided with a luer fitting which readily and quickly is attachable to an arthroscope. Moreover, the present invention includes a high pressure bleed valve assembly (HPBV) within the fluid circuit. The HPBV defines a support for connecting a first inflow fluid path, a second inflow fluid path, and a pressure monitor line. Under predetermined conditions, the pressure monitor line acts as the second inflow fluid path.

Ordinarily the first inflow fluid path communicates fluid to the joint and fluid pressure within the joint is communicated to the control unit via the pressure monitor line so that the control unit is capable of measuring the fluid pressure in the joint. In the event the first inflow fluid path is obstructed or closed at the arthroscope for whatever reason, it is possible with the HPBV to continue communication of fluid to the joint via the second inflow fluid path. This is possible because the HPBV is pressure responsive to open the first inflow fluid path to the second inflow fluid path and communicate fluid to the joint even though the first inflow fluid path may be obstructed downstream from the HPBV.

In addition, it is possible to provide fluid inflow communication to the joint via the first inflow fluid path and the second inflow fluid path in response to throttling fluid flow through the arthroscope.

It is an object of the present invention to incorporate further safety features into an irrigation system to avoid fluid leakage during set up and also to avoid unwanted pressure reduction in the joint during surgery.

In the drawings

Figure 1:
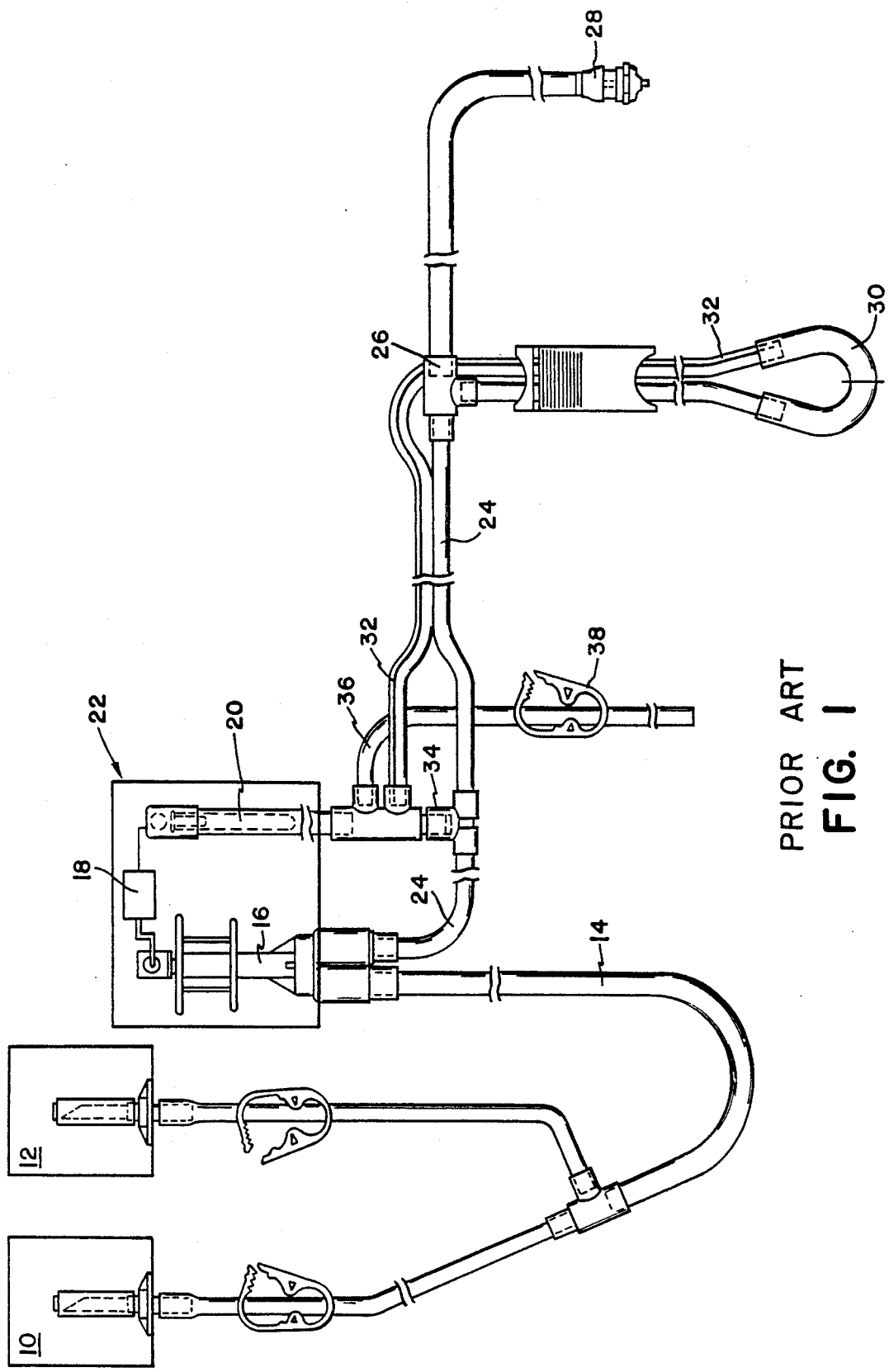
FIG. 1 is a schematic illustration of the fluid circuit of a prior art irrigation system.

In the prior art irrigation system of FIG. 1, a pair of bags 10 and 12 are filed with the fluid commonly used for irrigation during arthroscopy. These bags communicate via tubing 14 with a pump 16 which is operated by a motor 18 that is controlled by a pressure transducer 20. The pump 16, motor 18 and pressure transducer 20 comprise a control unit 22 such as described in U.S. Pat. No. 4,635,621 issued to Robert W. Atkinson on Jan. 13, 1987, and assigned to Snyder Laboratories, Inc. An outlet tubing 24 from the pump 16 communicates fluid to a junction 26 leading to a safety relief valve 28 and to a portion 30. The portion 30 communicates with a return tubing 32 leading from the portion 30 to the pressure transducer 20. A junction 34 intersects the tubing 24 and a bleed orifice (not shown) communicates fluid from the tubing 24 to the pressure transducer 20. A drain tubing 36 is provided at the pressure transducer 20 so that during a prime mode, the pump 16 is operable to fill all of the tubing with fluid from either bag 10 or 12. With all of the air evacuated via drain tube 36 and safety relief valve 28, the drain tubing 36 is closed via hand clamp 38 to maintain fluid in all of the tubing. At that time the portion 30 is cut to attach one cut end to an arthroscope 11, see FIG. 2, or to an inflow cannula and the other cut end to a pressure monitor cannula 13, see FIG. 2, so that arthroscopy of a joint is possible. The arthroscope 11 includes a stop cock 15 to control fluid flow through the arthroscope. Rotating the stop cock 15 opens and closes an inlet port for the arthroscope.

Figure 2:
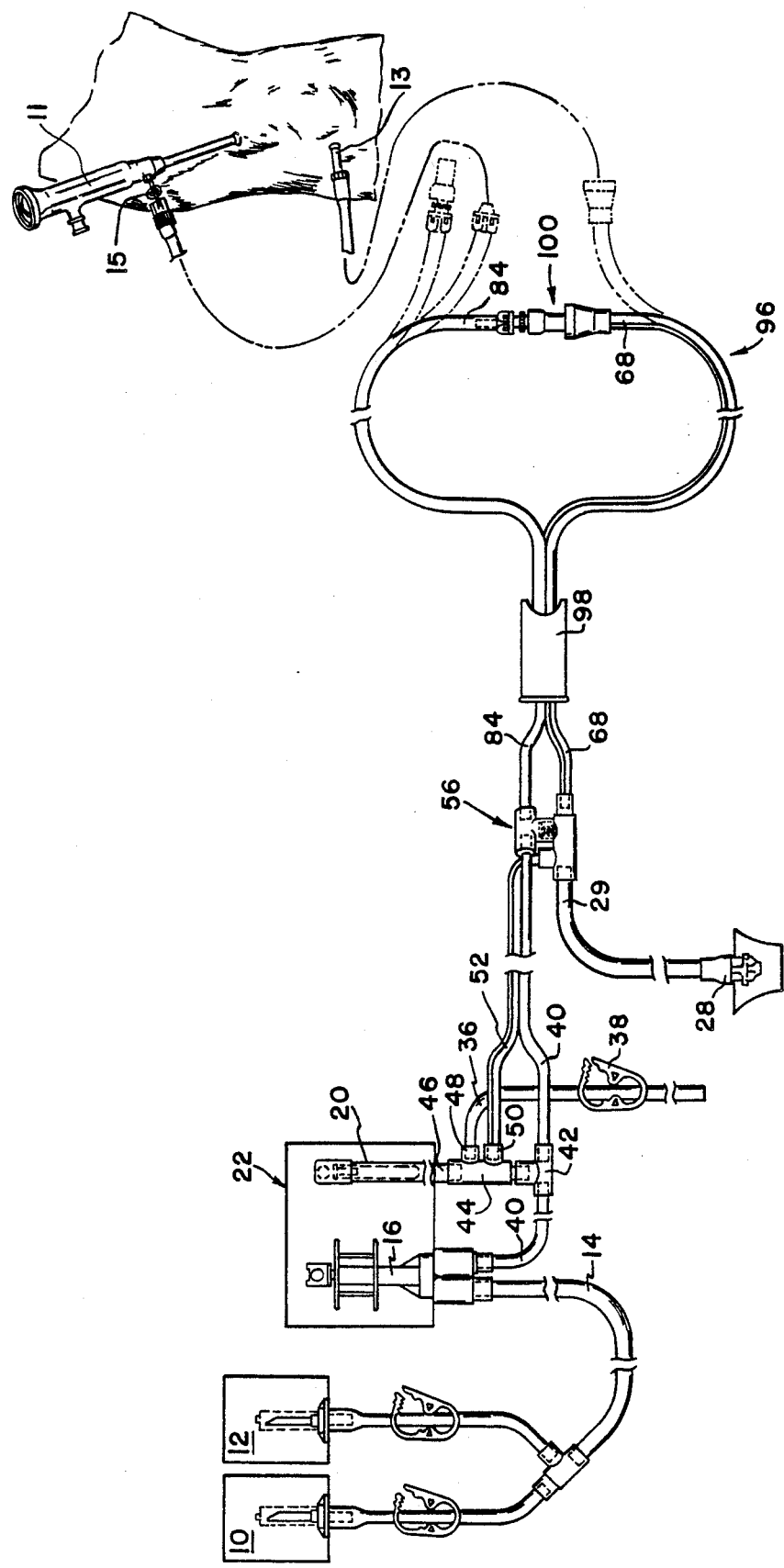
FIG. 2 is a schematic illustration of the irrigation system of the present invention.
Figure 3:
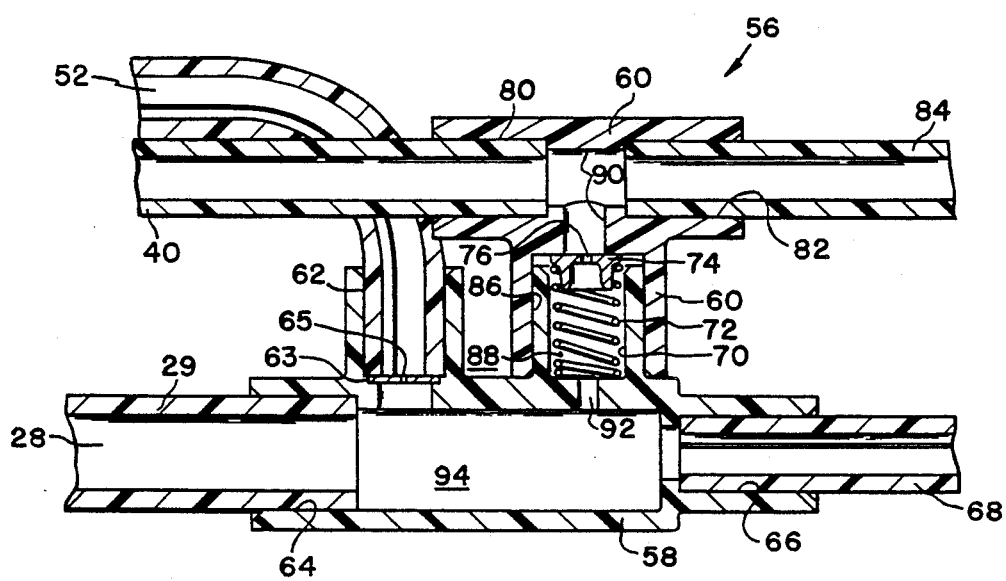
FIG. 3 is a cross-sectional view of the High Pressure Bleed Valve Assembly illustrated in FIG. 2.

Turning to the irrigation system of the present invention as illustrated in FIG. 2, similar components with FIG. 1 include the same reference numerals. Therefore, the fluid bags 10 and 12 communicate with the pump 16 of the control unit 22. An outlet tube 40 from the pump 16 connects with a junction 42. The junction 42 is attached to a fitting 44 having a first outlet 46 leading to the pressure transducer 20, a second outlet 48 leading to the drain tube 36 and a third outlet 50 receiving the return tube 52. The junction 42 intersects two legs of the outlet tube 40; however no communication is provided at the junction 42 between the outlet tube 40 and the pressure transducer 20. The outlet tube 40 leads to a High Pressure Bleed Valve Assembly (HPBV) 56, as shown more clearly in FIG. 3. The HPBV 56 includes a first section 58 and a second section 60 securely fastened together to form a plurality of ports or openings for fluid communication. The first section defines a first opening 62 communicating with the return tube 52 and a second opening 64 communicating via tube 29 with the safety relief valve 28. The safety relief valve is more fully described in U.S. Pat. No. 4,679,596 issued Jul. 14, 1987 to Dan Olson and assigned to Snyder Laboratories. A washer 63 disposed in the first opening 62 forms an orifice 65 to restrict fluid communication through return tube 52. The first section 58 further defines a third opening 66 communicating with a tube 68 and a fourth opening 70 receiving a spring 72 and a poppet 74 with a small bleed orifice 76. The spring 72 biases the poppet to sealingly engage the second section 60. The second section 60 defines a first opening 80 communicating with the outlet tube 40, a second opening 82 communicating with a tube 84, and a third opening 86 cooperating with the fourth opening 70 of the first section to form a chamber 88 receiving the spring 72 and poppet 74. As shown in FIG. 3, the second section forms a T-shaped opening 90 communicating tube 40 with tube 84 while also communicating these tubes with the chamber 88 via poppet 74 and orifice 76. The first section 58 defines an opening 92, communicating tubes 52, 29 and 68 with the chamber 88. A cavity 94 formed by the first section 58 provides open communication between openings 62, 64, 66 and 92.

Figure 4:
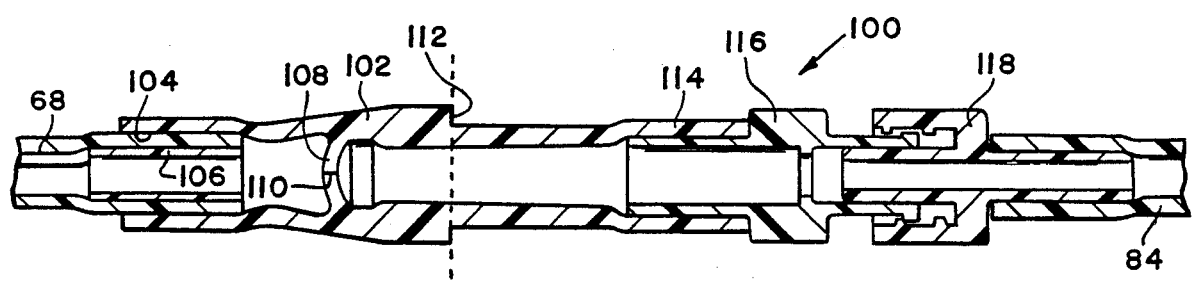
FIG. 4 is a cross-sectional view of the Monitor Check Valve Assembly illustrated is FIG. 2.

The tubes 68 and 84 lead away from the HPBV 56 to form a loop 96 beyond a clamp 98. A Monitor Check Valve Assembly (MCV) 100 is included within the loop 96, and is more clearly shown in FIG. 4. The MCV 100 defines a connector body 102 with a first opening 104 communicating with the end of tube 68. A tubular support 106 retains open fluid communication at the end of the tube 68. The connector body 102 forms a spherical membrane 108 with a slit 110 therein. The spherical membrane is sufficiently flexible to stretch in the direction of the tube 106 and open slit 110 in response to fluid pressure acting against the concave side of the spherical membrane. Moreover, fluid pressure acting against the convex side of the spherical membrane biases the latter to fluidly close the slit 110, provided such fluid pressure is minimal an outer shoulder 112 separates a tubular extension 114 from the part of the connector body 102 forming the spherical membrane 108. The tubular extension 114 receives a female luer 116 and a male luer 118 cooperates with the luer 116 to form a luer fitting communicating the connector body 102 with the tube 84.

With the irrigation system of the present invention set up in an operating room for arthroscopy of a joint, the control unit is set to a prime mode to evacuate air from the system. The clamp 38 and 98 are opened and fluid either bag 10 or 12 is communicated from the pump 16 to the tube 40, HPBV 56, tube 84, MCV 100, (the split 110 opens with fluid flow from tube 84 to tube 68) tube 68, HPBV 56 return tube 52, fitting 44 and drain tube 36. Fluid also communicates from the HPBV 56 to the safety relief valve 28 via tube 29. A suitable reservoir beneath the end of drain tube 36 and safety relief valve 28 collects excess fluid draining from the system when all of the air is evacuated. At this time the clamp 38 is closed to close the drain tube 36 and the control unit senses fluid pressure within the system via return tube 52 to stop further flow of fluid into the system. Next the surgeon cuts the MCV 100 at the outer shoulder 112. The portion of the MCV with the luer fitting forms a first end which is connected to an arthroscope via the male luer 118 after the female luer 116 and remaining tubular extension 114 are separated from the male luer 118. In the alternative, the remaining tubular extension 114 could be attached to a cannula if an arthroscope inflow is not used. The part of the MCV with the spherical membrane forms a second end following the cut. This second end can be neglected during joint diagnosis without leakage of fluid from tube 68 because the spherical membrane 108 closes the slit 110 in response to fluid pressure below a predetermined value acting against the convex side of the sphere.

Following diagnosis, or simultaneously with insertion of the arthroscope, the second end is connected to a cannular extending into the joint. The cannular bypasses the spherical membrane to retain the latter always open and defines a pressure monitor line. The surgeon sets the control unit to the desired pressure level to be maintained in the joint. Therefore, fluid communicated into the joint via tube 84 to pressurize and extend the joint is communicated from the joint via tube 68 to the pressure transducer 20 via HPBV 56 and return tube 52 to control the operation of the pump 16 and maintain the fluid pressure within the joint at the desired or predetermined pressure level.

In the event the flow of fluid through the arthroscope is closed, and fluid is drained from the joint to reduce the fluid pressure therein, it is possible to compensate for this drainage, as the pressure transducer senses the reduction in joint fluid pressure to activate pump 16. Fluid communicated to the HPBV is prevented from communicating further with the joint as the arthroscope is closed; however, the poppet 74 is opened against spring 72 in response to increasing fluid pressure within tubes 40 and 84 to communicate fluid from the pump to the joint via opening 76 and poppet 74, chamber 88, opening 92, cavity 94, tube 68 and the cannula bypassing the spherical membrane. In addition, the increasing fluid pressure opening poppet 74 is communicated to the return tube 52 for communication with the pressure transducer 20 to control operation of the pump 16, as well as communicating with the safety relief valve assembly 28 via cavity 94 and tube 29 to prevent too high a pressure level within the joint.

With the present invention, the surgeon can partially close the arthroscope stop cock and provide for dual flow through the arthroscope, albeit restricted, and through the tube 68 with the poppet 74 opened. Moreover, the surgeon can completely close the stop cock on the arthroscope and provide for fluid communication to the joint solely through tube 68.

With the aforegoing irrigation system, the surgeon can readily and quickly connect an arthroscope and cannula for arthroscopy of a joint with minimal fluid leakage. Moreover, the surgeon can control fluid flow to the joint via the arthroscope or via the MCV tube 68, or both. The HPBV prioritizes fluid flow to the loop during the prime mode to evacuate the loop of air and the HPBV prioritizes fluid flow to the joint during surgery to maintain a predetermined fluid pressure level within the joint.

I claim:

1. An irrigation system for arthroscopy of a joint comprising a fluid circuit communicating with a fluid reservoir, means for pressurizing the fluid within the fluid circuit to generate fluid flow within the fluid circuit, the fluid circuit having means separable at a predetermined location to define a first end adapted for communicating the fluid circuit into the joint via a first cannula connected to the first end and extending into the joint and a second end adapted for communicating the fluid circuit into the joint via a second cannula connected to the second end and extending into the joint, the first and second cannula extending into the joint, and the fluid circuit includes a monitor check valve assembly near the predetermined location which is open during a prime mode to permit fluid communication therethrough in order to fill the fluid circuit with fluid before the fluid circuit is separated, the monitor check valve assembly being closed immediately following separation to trap fluid downstream thereof in the fluid circuit, and the monitor check valve assembly providing the fluid communication from the joint to the fluid circuit downstream of the second end when the fluid circuit is separated and the second end is connected to the second cannula to open the monitor check valve assembly.

2. The irrigation system of claim 1 in which the fluid circuit defines a loop downstream of a clamp, the clamp being disposed downstream of the reservoir and being closed to isolate the loop from the remaining portion of the fluid circuit and the monitor check valve assembly is disposed within the loop of the fluid circuit.

3. The irrigation system of claim 1 in which the fluid circuit includes a luer fitting providing fluid communication therethrough prior to separation of the fluid circuit near the luer fitting whereby the luer fitting defines the first end for connection to the first cannula.

4. An irrigation system for arthroscopy of a joint comprising a fluid circuit communicating with a fluid reservoir, means for pressurizing the fluid within the fluid circuit to generate fluid flow within the fluid circuit, the fluid circuit having means separable at a predetermined location to define a first end adapted for communicating the fluid circuit into the joint via a first cannula connected to the first end and extending into the joint and a second end adapted for communicating the fluid circuit into the joint via a second cannula connected to the second end and extending into the joint, the first and second cannula extending into the joint, and the fluid circuit includes a monitor check valve assembly near the predetermined location which is open during a prime mode to permit fluid communication therethrough in order to fill the fluid circuit with fluid before the fluid circuit is separated, the monitor check valve assembly being closed immediately following separation to trap fluid downstream thereof in the fluid circuit, and the monitor check valve assembly providing for fluid communication from the joint to the fluid circuit downstream of the second end when the fluid circuit is separated and the second end is connected to the second cannula to open the monitor check valve, the fluid circuit including a luer fitting providing fluid communication therethrough prior to separation of the fluid circuit near the luer fitting whereby the luer fitting defines the first end for connection to the first end, and the separation of the fluid circuit is between the luer fitting and the monitor check valve assembly.

5. An irrigation system for use during arthroscopy of a joint comprising a fluid circuit with means for communicating fluid through the fluid circuit, the fluid circuit initially defines a closed fluid loop to permit communication of fluid from a reservoir to the communicating means and throughout the entire fluid circuit, the fluid circuit having means separable at a predetermined location to define first and second ends, the first end connecting with a first cannula extending into the joint which permits visual inspection of the joint and also communicates fluid from the reservoir to the joint to pressurize the latter, the fluid circuit including a first valve member near the second end to substantially eliminate leakage of fluid from the fluid circuit when the fluid circuit is connected to only the first cannula, and the fluid circuit including a second valve member between the reservoir and the predetermined location permitting fluid communication from the reservoir to the joint via a second cannula extending into the joint and connected to the second end to bypass the first valve member.

6. An irrigation system for arthroscopy of a joint comprising a fluid circuit which initially defines a fluid loop, means for communicating fluid through the fluid circuit during a prime mode to evacuate air from the fluid circuit and fill the latter with fluid, the fluid circuit having means separable at a predetermined location for attachment to a first cannula and a second cannula which both extend into the joint, the fluid circuit at the predetermined location including a fitting assembly which communicates fluid therethrough during the prime mode and is adapted for ready attachment to the first cannula following separation at the predetermined location, the separated fluid circuit forming a first end connected to the first cannula and a second end connected to the second cannula, the first end including the fitting assembly and the second end including a valve assembly normally preventing fluid flow outwardly from the second end before the latter is connected to the second cannula.

* * * * *